United States Patent [19]

Gill et al.

[11] Patent Number: 4,808,215

[45] Date of Patent: Feb. 28, 1989

[54] METHOD OF IMPROVING THE FLOWABILITY OF AGRO-CHEMICAL SLURRIES

[75] Inventors: Jasbir S. Gill; Richard G. Varsanik, both of Coraopolis, Pa.

[73] Assignee: Calgon Corporation, Pittsburgh, Pa.

[21] Appl. No.: 34,826

[22] Filed: Apr. 3, 1987

Related U.S. Application Data

[63] Continuation of Ser. No. 791,670, Oct. 28, 1985, abandoned.

[51] Int. Cl.$^4$ .............................................. A01N 37/34
[52] U.S. Cl. ........................................ 71/105; 71/112; 71/DIG. 1
[58] Field of Search ........... 514/525; 71/105, DIG. 1, 71/112

[56] References Cited

U.S. PATENT DOCUMENTS

| | | | |
|---|---|---|---|
| 2,923,634 | 2/1960 | Lindemann | 71/112 |
| 3,331,735 | 7/1967 | Battershell et al. | 514/525 |
| 3,806,485 | 4/1974 | Frisque | 71/DIG. 1 |
| 4,242,356 | 12/1980 | Hasegawa et al. | 514/525 |
| 4,411,693 | 10/1983 | LeClair et al. | 71/DIG. 1 |

OTHER PUBLICATIONS

McCutcheons Detergents & Emulsifiers, p. 192 (1971).

Primary Examiner—Glennon H. Hollrah
Assistant Examiner—A. A. Owens
Attorney, Agent, or Firm—W. C. Mitchell; M. C. Sudol, Jr.

[57] ABSTRACT

The instant invention is directed to compositions and a method of improving the flowability of agro-chemical slurries and suspensions, comprising adding to the suspension or slurry being treated an effective amount of: (a) a water soluble polymer; and, optionally, (b) a surfactant, wherein the polyelectrolyte/surfactant weight ratio ranges from 10:1 to 1:10.

4 Claims, No Drawings

METHOD OF IMPROVING THE FLOWABILITY OF AGRO-CHEMICAL SLURRIES

This is a continuation of application Ser. No. 791,670, filed Oct. 28, 1985, now abandoned.

BACKGROUND OF THE ART

The instant invention relates to compositions and a method for improving the flowability of slurries and suspensions of agro-chemicals. More particularly, this invention relates to the use of water soluble polymers and, optionally, surfactants to reduce the sedimentation and caking of agro-chemicals. Sedimentation and caking of agro-chemicals, especially herbicides, present severe handling problems.

The presence of the additives disclosed herein makes sedimented cakes very soft, so that they can be easily redistributed into a liquid phase to form a homogeneous slurry or suspension. Additionally, the instant additives assist in keeping agro-chemical solids in suspension.

Settling, as used herein, is defined as the separation of a slurry or suspension into components having greater and lesser concentrations of the solid or solids than does the original slurry or suspension. As such, the terms settling, sedimentation, and separation are synonomous and interchangeable.

Suspensions and slurries are defined as liquid-solids systems wherein the solids are dispersed or entrained in a liquid. For example, slurries or suspensions may comprise water as the liquid and an agro-chemical as the solid.

Agro-chemicals include any compound used to assist plant growth, such as herbicides, insecticides and fertilizers. The inventors have found that, by adding specified water soluble polymers and/or surfactants to agro-chemical suspensions, at designated dosages, settling of the solid phase is inhibited. Additionally, cakes which do form are softened by the additives and easily redistributed into the liquid phase. This improves the flowability of agro-chemical slurries and suspensions, thereby minimizing treatment costs.

DETAILED DESCRIPTION OF THE INVENTION

The instant invention is directed to a method of improving the flowability of an agro-chemical suspension comprising adding to said suspension an effective amount of (a) a water soluble polymer selected from the group consisting of: polymers of acrylic acid, methacrylic acid, alpha-halo-acrylic acid, maleic, acid or anhydride, itaconic acid, vinyl acetic acid, allylacetic acid, fumaric acid, $\beta$-carboxyethyl acrylate and crotonic acid, alone or in combination, and salts thereof; polymers of acrylic acid and polymerizable unsaturated water-soluble monomers selected from the group consisting of polyethylene glycol mono methacrylate, 2-hydroxypropyl acrylate, vinyl sulfonic acid, vinyl phosphonic acid, vinyl acetate, ethyl vinyl ether, acrylamide, ethyl acrylate, ethyl ethacrylate, methacrylamide, 2-acrylamido-2-methylpropyl sulfonic acid, 2-methacrylamido-2-methylpropyl sulfonic acid, styrene sulfonic acid, sulfoalkyl acrylate, sulfoalkyl methacrylate, allyl sulfonic acid, methallyl sulfonic acid, and 3-methacrylamido-2-hydroxy-propyl sulfonic acid, alone or in combination, their salts and mixtures thereof; polymers of methacrylic acid and polymerizable unsaturated water-soluble monomers selected from the group consisting of polyethylene glycol mono methacrylate, 2-hydroxypropyl acrylate, vinyl sulfonic acid, vinyl phosphonic acid, vinyl acetate, ethyl vinyl ether, acrylamide, ethyl acrylate, ethyl methacrylate, methacrylamide, 2-acrylamido-2-methylpropyl sulfonic acid, 2-methacrylamido-2-methylpropyl sulfonic acid, styrene sulfonic acid, sulfoalkyl acrylate, sulfoalkyl methacrylate, allyl sulfonic acid, methallyl sulfonic acid, and 3-methacrylamido-2-hydroxy-propyl sulfonic acid, alone or in combination, their salts and mixtures thereof; polymers of acrylamide which are partially hydrolized; polymers of dimethyldiallyl ammonium chloride and/or diethyldiallyl ammonium chloride; and polyethylene imine; and, optionally, (b) a surfactant selected from the group consisting of alkyl sulfonates, aryl sulfonates, alkylaryl sulfonates, sulfosuccinates, sulfoesters of fatty acids, sulfated alcohols, sulfated esters, ethoxylated alcohol sulfates, sulfated alkylphenol ethoxylates, and phosphate esters; wherein the polyelectrolyte/surfactant weight ratio ranges from 10:1 to 1:10. Optimally, the polymer/surfactant weight ratio ranges from 5:1 to 1:1.5.

The instant invention is further directed to a composition comprising: (a) an agro-chemical slurry or suspension; (b) a water-soluble polymer; and, optionally, (c) a surfactant, wherein said composition is readily flowable and easily homogenized, and wherein the dosage of said polymer in said slurry or suspension is at least 0.1 ppm.

Agro-chemical slurries or suspensions, as used herein, refer to aqueous suspensions of herbicides, pesticides, fertilizers and the like. The instant method is especially effective for use with herbicide suspensions, such as suspensions comprising 1,4-benzenedicarboxylic acid-2,3,5,6-tetrachloromethyl ester or 1,3-benzenecarbonitrile-2,4,5,6-tetrachloro and water.

Water-soluble polymers, as used herein, include polymers that carry negatively or positively charged groups along the polymer chain. The preferred anionic water-soluble polymers employed in the compositions and method of the instant invention are polymers of any unsaturated carboxylic acid, or salts thereof. As examples of these preferred anionic polymers, there may be mentioned: polymers of acrylic acid, methacrylic acid, alpha-halo-acrylic acid, maleic acid or anhydride, itaconic acid, vinyl acetic acid, allylacetic acid, fumaric acid, $\beta$-carboxyethyl acrylate and crotonic acid, alone or in combination, and salts thereof. Also preferred are polymers of acrylic acid and/or methacrylic acid with other polymerizable unsaturated water-soluble monomers, including but not limited to, polyethylene glycol mono methacrylate, 2-hydroxypropyl acrylate, vinyl sulfonic acid, vinyl phosphonic acid, vinyl acetate, ethyl vinyl ether, acrylamide, ethyl acrylate, ethyl methacrylate, methacrylamide, 2-acrylamido-2-methylpropyl sulfonic acid, 2-methacrylamido-2-methylpropyl sulfonic acid, styrene sulfonic acid, sulfoalkyl acrylate, sulfoalkyl methacrylate, allyl sulfonic acid, methallyl sulfonic acid, and 3-methacrylamido-2-hydroxypropyl sulfonic acid, alone or in combination, their salts and mixtures thereof. Also included in this class of polymers are those polymers of acrylamide which are partially hydrolyzed.

The preferred cationic water soluble polymers include polymers prepared from dimethyldiallyl ammonium chloride (DMDAAC) and diethyldiallyl ammonium chloride (DEDAAC), alone or in combination, and polyethylene imine.

The molecular weight of the polymer used is not critical. The preferred polymers have molecular weights of from about 1,000 to about 5,000,000 and the more preferred polymers have molecular weights of from about 1,000 to about 1,000,000, as determined by light scattering techniques. The most preferred polymers have molecular weights of from about 1000 to about 100,000.

As specific examples of preferred anionic water soluble polymers there may be mentioned: homopolymers of acrylic acid, homopolymers of methacrylic acid, copolymers of acrylic acid and methacrylic acid, copolymers of acrylic acid and 2-acrylamido-2-methyl propyl sulfonic acid or 2-methacrylamido-2-methylpropyl sulfonic acid, copolymers of methacrylic acid and 2-acrylamido-2-methyl propyl sulfonic acid or 2-methacrylamido-2-methylpropyl sulfonic acid, copolymers of acrylic acid and 2-hydroxypropyl acrylate, copolymers of methacrylic acid and 2-hydroxypropyl acrylate, poly maleic acid, copolymers of maleic acid or anhydride and sulfonated styrene, copolymers of maleic acid or anhydride and acrylic acid or methacrylic acid, copolymers of acrylic acid or methacrylic acid and acrylamide or methacrylamide, terpolymers of acrylic acid, 2-acrylamido-2-methyl propyl sulfonic acid or 2-methyacrylamido-2-methylpropyl sulfonic acid and polyethylene glycol mono methacrylate, and terpolymers of methacrylic acid, 2-acrylamido-2-methylpropyl sulfonic acid or 2-methacrylamido-2-methylpropyl sulfonic acid and polyethylene glycol mono methacrylate, and homologs thereof.

As specific examples of preferred cationic polymers, there may be mentioned homopolymers of DMDAAC, homopolymers of DEDAAC, copolymers of DMDAAC and DEDAAC and polyethylene imines.

The second component which may optionally be used in the instant method and compositions is a surfactant. Surfactants, as used herein, are defined as compounds having a charged surface-active moiety. Any surfactant can be used. Preferred surfactants include, but are not limited to, sulfonates, sulfates, phosphates, and succinates. Further, sodium and potassium salts of these surfactants are also acceptable due to their greater solubility in water. More preferred are anionic surfactants which include, but are not limited to, alkyl, aryl and alkylaryl sulfonates, sulfosuccinates, sulfoesters of fatty acids, sulfated alcohols, sulfated esters, ethoxylated alcohol sulfates, sulfated alkyl phenol ethoxylates, and phosphate esters.

Preferred succinates are dialkylsulfosuccinates and ethoxylated alcohol half esters or ethoxylated nonylphenol half esters of sulfosuccinic acid, and their salts. This class includes, but is not limited to, sodium di(2-ethyl-hexyl)sulfosuccinate, dioctylsulfosuccinate, diisobutylsulfosuccinate, dihexylsulfosuccinate, diamylsulfosuccinate, disodium ethoxylated alcohol half ester of sulfosuccinic acid and disodium ethoxylated nonyl phenol half ester of sulfosuccinic acid. Another preferred succinate is polyethyleneoxysulfosuccinate. Examples of preferred succinates are Aerosol A-102 and Aerosol A-103, available from American Cyanamid Company.

The preferred sulfated surfactants are sulfated polyoxyethylene alkylphenols. The preferred phosphate esters are alkylorthophosphates such as butyl phosphate, hexyl phosphate, 2-ethylhexyl phosphate, octyl phosphate, decyl phosphate, octyldecyl phosphate, mixed allyl phosphates, and alkyl polyphosphates, such as hexyl polyphosphate, and octyl polyphosphate, polyphosphated alcohols, ethoxylated and phosphated alkyl alcohols, and ethoxylated and phosphated alkyl phenols, or salts thereof, especially sodium and potassium salts. Another preferred phosphate surfactant is octylphenoxypolyethoxyethylphosphate, or its sodium or potassium salts.

An example of a preferred phosphate ester salt is Triton H-66, available from Rohm & Haas Company.

The weight ratio of the water soluble polymer to surfactant, if used, should be 10:1 to 1:10, on a weight:weight basis, preferably 5:1 to 1:1.5, and most preferably from 1.5:1 to 1:1.5.

The term "effective amount" of the instant additives disclosed herein means that dosage of the additive necessary to inhibit settling of agro-chemicals from the suspension being treated, or that dosage which will soften a settled cake. Treatment levels from about 0.1 to as high as 1000 ppm may be used (based on the total weight of the slurry or suspension being treated), depending on the concentration of solids in the suspension and the temperature of the suspension. The preferred treatment level is from 0.1 to 100 ppm, based on the total weight of the suspension or slurry being treated, and the most preferred treatment level is from 1 to 50 ppm. Typically, agro-chemical slurries or suspensions are aqueous and contain 2 to 10%, by weight, solids. Slurries containing higher solids concentrations may require higher dosages.

The preferred compositions comprise: (a) an agrochemical-water slurry or suspension; (b) a water soluble polymer having a weight average molecular weight of from about 1000 to about 100,000, as determined by light scattering techniques, selected from the group consisting of DMDAAC polymers, DEDAAC polymers, DMDAAC and DEDAAC polymers, polyethylene imines and polymers prepared from an unsaturated carboxylic acid selected from the group consisting of acrylic acid, methacrylic acid, @-haloacrylic acid, maleic acid or anhydride, vinylacetic acid, allylacetic acid, fumaric acid, and β-carboxyethyl-acrylate, alone or in combination, and an unsaturated sulfonic acid selected from the group consisting of 2-acrylamido-2-methylpropylsulfonic acid, 2-methacrylamido-2-methylpropylsulfonic acid, vinylsulfonic acid, sulfoalkyl acrylate, sulfoalkyl methacrylate, allylsulfonic acid, methallylsulfonic acid, and 3-methacrylamido-2-hydroxypropylsulfonic acid, alone or in combination, and salts and mixtures of these polymers, wherein the carboyxlic/sulfonic weight ratio ranges from 1:20 to 20:1; and, optionally, (c) a surfactant selected from the group consisting of alkylorthophosphates, alkylpolyphosphates, octylphenoxypolyethoxy-ethylphosphates, sulfosuccinates, esters of sulfosuccinates and salts thereof, alone or in combination, wherein the weight ratio of component (b) to component (c), if used, is 10:1 to 1:5. More preferably, this ratio is 5:1 to 1:1.5, and most preferably 1.5:1 to 1:1.5. Though it is preferred that the water-soluble polymers and surfactants (when used) of this invention be combined and utilized as compositions, they may be added separately without departing from the spirit of the invention.

The most preferred additives are selected from the group consisting of polyethylene imines, DMDAAC polymers, DEDAAC polymers, and polymers of DMDAAC and DEDAAC, alone or in combination.

EXAMPLES

The following examples illustrate the present invention in greater detail. It should be understood, however, that these examples in no way limit the present invention.

In Examples 1-48, additives were evaluated using a low solids suspension, comprising water and 5.0 g/l Dacthal 6F. Dacthal 6F is 1,4-benzenedicarboxylic acid-2,3,5,6-tetrachloro dimethyl ester, which is available from S.D.S. Biotech Corp., Cleveland, Ohio as a herbicide. Dosages are based on the total suspension weight.

The suspensions of the examples were allowed to stand for the times shown. The values appearing in the last column of Table 1 indicate the number of inversions required for 100% homogeneity, after standing. The additives were added to the suspensions prior to standing.

In the Examples:

SPA-410=a 1:1 weight ratio admixture of AA-/AMPSA AND H-66, available from Calgon Corporation, Pittsburgh, PA.

AA=polyacrylic acid, MWT=4700, as determined by light scattering.

AA/AMPSA=copolymers of acrylic acid and 2-acrylamido-2-methylpropyl sulfonic acid ahving a weight average molecular weight of about 8200, as determined by low angle light scattering.

PMA=polymaleic acid, MWT=1300, as determined by light scattering, 70% active.

PEO=allyl polyethylene oxide, available from Corbova Chemical.

DMDAAC=polydimethyldiallyl ammonium chloride, MWT=130,000, as determined by light scattering.

PEI=polyethylene imine, available from Cordova Chemical.

H-66=Triton H-66, a potassium salt of phosphate ester, available from Rohm and Haas Company.

J-2=Amphoterge J-2, a substituted imidazoline available from Lonza.

A-103=Aerosol A-103, a disodium ethoxylated. nonyl phenol half ester of sulfosuccinic acid, available from American Cyanamide Company.

HEDP=hydroxyethylidene diphosphonic acid.

HYPAM=hydrolyzed polyacrylamide, available from American Cyanamide Company.

Results are shown in Table I.

TABLE I

| Example No. | Additive | Dosage (ppm) | Standing Time (Hours) | Number of Inversions for 100% Homogeneity, 5.0 g/l DACTHAL 6F |
|---|---|---|---|---|
| 1* | — | — | 43 | 56 |
| 2 | SPA-410 | 2 | 43 | 48 |
| 3 | SPA-410 | 5 | 43 | 60 |
| 4 | SPA-410 | 10 | 43 | 49 |
| 5 | SPA-410 | 20 | 43 | 40 |
| 6 | SPA-410 | 50 | 43 | 46 |
| 7* | — | — | 23 | 43 |
| 8 | AA | 50 | 23 | 35 |
| 9 | AA-AMPSA | 50 | 23 | 25 |
| 10 | PMA | 50 | 23 | 40 |
| 11 | PEO | 50 | 23 | 38 |
| 12 | DMDAAC | 50 | 23 | 29 |
| 13* | — | — | 20.5 | 40 |
| 14 | AA | 100 | 20.5 | 39 |
| 15 | AA-AMPSA | 100 | 20.5 | 34 |
| 16 | PMA | 100 | 20.5 | 37 |
| 17 | PEO | 100 | 20.5 | 31 |
| 18 | DMDAAC | 100 | 20.5 | 30 |
| 19 | PEI/AA-AMPSA | 50/50 | 21.5 | 6 |
| 20 | HEDP/AA-AMPSA | 5/50 | 21.5 | 31 |
| 21 | AA/H-66 | 50/50 | 21 | 37 |
| 22 | AA/J-2 | 50/50 | 21 | 44 |
| 23 | AA/A-103 | 50/50 | 21 | 42 |
| 24 | AA-AMPSA/H-66 | 50/50 | 21 | 37 |
| 25 | AA-AMPSA/J-2 | 50/50 | 21 | 32 |
| 26 | AA-AMPSA/A-103 | 50/50 | 21 | 34 |
| 27 | PMA/H-66 | 50/50 | 21 | 46 |
| 28 | PMA/J-2 | 50/50 | 21 | 38 |
| 29 | PMA/A-103 | 50/50 | 21 | 35 |
| 30+ | PEI/AA-AMPSA | 50/50 | 20.5+ | 20 |
| 31 | PEI | 50 | 22 | 9 |
| 32 | PEI/AA-AMPSA | 25/25 | 22 | 25 |
| 33 | PEI/AA | 25/25 | 22 | 24 |
| 34 | PEI/H-66 | 25/25 | 22 | 10 |
| 35 | PEI/A-103 | 25/25 | 22 | 20 |
| 36 | PEI/H-66 | 10/40 | 25 | 12 |
| 37 | PEI/H-66 | 40/10 | 25 | 16 |
| 38 | PEI/H-66 | 17/33 | 25 | 12 |
| 39 | PEI/H-66 | 33/17 | 25 | 11 |
| 40 | PEI/H-66 | 20/10 | 24 | 11 |
| 41 | PEI/H-66 | 3/7 | 24 | 11 |
| 42 | PEI/H-66 | 7/3 | 24 | 14 |
| 43 | PEI | 30 | 23 | 8 |
| 44 | PEI/H-66 | 33/17 | 23 | 10 |
| 45 | PEI/AA-AMPSA | 33/17 | 23 | 8 |
| 46+ | PEI | 50 | 23 | 4 |
| 47+ | PEI/H-66 | 33/17 | 23 | 40 |
| 48+ | PEI/AA-AMPSA | 33/17 | 23 | 4 |

*Comparison examples
+ Refrigerated samples

In Examples 49-109, tests similar to tests 1-48 were run using Bravo 500, a 1,3-benzene, carbonitrile-2,4,5,6 tetrachloro available from S.D.S Biotech Corp. Results are shown below in Table II.

TABLE II

| Example No. | Additive | Dosage (ppm) | Standing Time (Hours) | Number of Inversions for 100% Homogeneity, 5.0 g/l BRAVO 500 |
|---|---|---|---|---|
| 49* | — | — | 22 | 70 |
| 50 | SPA-410 | 2 | 22 | 63 |
| 51 | SPA-410 | 5 | 22 | 64 |
| 52 | SPA-410 | 10 | 22 | 76 |
| 53 | SPA-410 | 20 | 22 | 64 |
| 54 | SPA-410 | 50 | 22 | 68 |
| 55 | PEI/AA-AMPSA | 50/50 | 20.5 | 25 |
| 56* | — | — | 21.5 | 74 |
| 57 | AA/H-66 | 50/50 | 21.5 | 79 |
| 58 | AA/A-103 | 50/50 | 21.5 | 82 |
| 59 | AA/J-2 | 50/50 | 21.5 | 71 |
| 60 | AA-AMPSA/H-66 | 50/50 | 21.5 | 76 |
| 61 | AA-AMPSA/A-103 | 50/50 | 21.5 | 86 |
| 62 | AA-AMPSA/J-2 | 50/50 | 21.5 | 74 |
| 63 | PMA/H-66 | 50/50 | 21.5 | 79 |
| 64 | PMA/A-103 | 50/50 | 21.5 | ˙77 |
| 65 | PMA/J-2 | 50/50 | 21.5 | 82 |
| 66 | PEO/H-66 | 50/50 | 23 | 77 |
| 67 | PEO/A-103 | 50/50 | 23 | 73 |
| 68 | PEO/J-2 | 50/50 | 23 | 72 |
| 69 | DMDAAC/H-66 | 50/50 | 23 | 21 |
| 70 | DMDAAC/A-103 | 50/50 | 23 | 15 |
| 71 | DMDAAC/J-2 | 50/50 | 23 | 15 |
| 72 | PEI/H-66 | 50/50 | 23 | 21 |

TABLE II-continued

| Example No. | Additive | Dosage (ppm) | Standing Time (Hours) | Number of Inversions for 100% Homogeneity, 5.0 g/l BRAVO 500 |
|---|---|---|---|---|
| 73 | PEI/AA-AMPSA | 50/50 | 23 | 17 |
| 74 | PEI | 50 | 23 | 15 |
| 75 | PEI/H-66 | 25/25 | 22 | 5 |
| 76 | PEI/A-103 | 25/25 | 22 | 7 |
| 77 | PEI | 25 | 22 | 3 |
| 78 | PEI | 50 | 22 | 3 |
| 79 | PEI | 25 | 22 | 2 |
| 80 | PEI | 50 | 22 | 6 |
| 81 | PEI | 25 | 22 | 2 |
| 82 | PEI | 20 | 24 | 5 |
| 83 | PEI | 20 | 24 | 3 |
| 84 | PEI/A-103 | 20/20 | 24 | 13 |
| 85 | PEI/A-103 | 20/20 | 24 | 9 |
| 86 | PEI | 20 | 21 | 2 |
| 87 | DMDAAC | 20 | 21 | 4 |
| 88 | PEI/A-103 | 20/20 | 21 | 4 |
| 89 | HYPAM | 100 | 23 | 70 |
| 90 | HYPAM | 50 | 23 | 70 |
| 91 | HYPAM | 25 | 23 | 70 |
| 92 | HYPAM/J-2 | 50/50 | 22.5 | 70 |
| 93 | HYPAM/J-2 | 50/25 | 22.5 | 70 |
| 94 | HYPAM/J-2 | 25/50 | 22.5 | 70 |
| 95 | HYPAM/H-66 | 50/50 | 22.5 | 70 |
| 96 | HYPAM/H-66 | 50/25 | 22.5 | 70 |
| 97 | HYPAM/H-66 | 25/50 | 22.5 | 70 |
| 98 | PEI | 25 | 22 | 2 |
| 99 | PEI | 25 | 22 | 3 |
| 100 | PEI/H-66 | 25 | 22 | 3 |
| 101 | PEI/AA-AMPSA | 25 | 22 | 23 |
| 102 | PEI/A-103 | 25 | 22 | 3 |
| 103 | DMDAAC/AA-AMPSA | 25/25 | 22 | 20 |
| 104 | DMDAAC/A-103 | 25/25 | 22 | 35 |
| 105 | DMDAAC/A-103 | 25/25 | 22 | 3 |
| 106 | DMDAAC/A-103 | 25/25 | 22 | 30 |
| 107 | PEI | 25 | 22 | 2 |
| 108 | PEI/AA-AMPS | 25/25 | 22 | 39 |
| 109 | DMDAAC/A-103 | 25/25 | 22 | 3 |

What is claimed is:

1. A method of improving the flowability of a herbicide suspension comprising adding to said suspension an effective amount of a polyethylene imine, wherein said herbicide suspension comprises: (i) a herbicide selected from the group consisting of 1, 4-benzenedicarboxylic acid-2, 3, 5, 6-tetrachloro dimethyl ester and 1, 3-benzenecarbonitrile-2, 4, 5, 6 tetrachloro; and (ii) water.

2. The method of claim 1, wherein said effective amount ranges from 0.1 to 1000 ppm, based on the total weight of said suspension.

3. The method of claim 1, wherein said effective amount ranges from 0.1 to 100 ppm, based on the total weight of said suspension.

4. A composition comprising: (a) a herbicide suspension comprising (i) a herbicide selected from the group consisting of 1,4-benzenedicarboxylic acid-2, 3, 5, 6-tetrachloro dimethyl ester and 1,3-benzenecarbonitrile-2, 4, 5, 6-tetrachloro; and (ii) water; and (b) a polyethylene imine, wherein at least 0.1 ppm of said poyethylene imine is present, based on the total weight of (a).

* * * * *